United States Patent
Apffel, Jr. et al.

(10) Patent No.: US 7,109,040 B2
(45) Date of Patent: Sep. 19, 2006

(54) MODULAR ISOTOPE CODING APPROACH TO PROTEOMIC ANALYSIS

(75) Inventors: James Alexander Apffel, Jr., Mountain View, CA (US); Karla M. Robotti, Mountain View, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 444 days.

(21) Appl. No.: 10/318,475

(22) Filed: Dec. 13, 2002

(65) Prior Publication Data

US 2005/0100956 A1 May 12, 2005

(51) Int. Cl.
*G01N 24/00* (2006.01)
*C07K 1/13* (2006.01)
*C07K 1/14* (2006.01)
*C07K 1/16* (2006.01)

(52) U.S. Cl. .................. 436/173; 530/403; 530/412; 530/344; 436/86

(58) Field of Classification Search ............... 436/544, 436/161, 545, 173, 176; 544/198, 209, 180; 530/403, 412, 344; 564/281
See application file for complete search history.

(56) References Cited

U.S. PATENT DOCUMENTS

2002/0037532 A1 3/2002 Regnier et al.
2002/0168691 A1* 11/2002 Becker .................. 435/7.5

FOREIGN PATENT DOCUMENTS

| WO | WO97/10887 | 9/1996 |
| WO | WO00/11208 | 8/1999 |
| WO | WO04/015391 A2 | 8/2003 |

OTHER PUBLICATIONS

Geng, J. et al., "Signature-peptide approach to detecting proteins in complex mixtures", Chrom. A., vol. 870, (2000), pp. 295-313.

Stankova, M., et al., "Library Generation through successive substitution of trichlorotriazine", Molecular Diversity, Escom Science Publishers, Leiden, NL, vol. 2, No. 1/2, 1996, pp. 75-80.

Gustafson, G. R., et al., "Incorporation of Carbohydrates and Peptides into Large Triazine-Based Screening Libraries Using Automated Parallel Synthesis"; Tetrahedron, Elsevier Science Publishers, Amsterdam, NL, vol. 54, No. 16, Apr. 16, 1998, pp. 4051-4065.

Scham, D., et al., "Spatially addressed synthesis of amino- and amino-oxy-substituted 1, 3, 5-triazine arrays on polymericmembranes", Journal of Combinatorial Chemistry, American Chemical Society, Washington, US vol. 2, Jun. 2000, pp. 361-369.

Yamada, H., et al., "An S-Alkylating Reagent with positive charges as an efficient solubilizer of Denatured Disulfide-containing proteins", Journal of Biochemistry, Japanes Biochemical Society, Tokyo, JP, vol. 116, 1994, pp. 852-857.

* cited by examiner

*Primary Examiner*—Molly E. Ceperley
*Assistant Examiner*—Shafiqul Haq

(57) ABSTRACT

The present invention provides methods for analyzing a peptide or peptides of interest in a protein sample using a combination of a relatively generic isotope tag with a decoupled selection process, allowing simplified customization of the application with a single reagent. These methods comprise providing a first and a second protein sample; labeling the first protein sample with a first Universal Peptide Isotope Tag (U-PIT) reagent and the second protein sample with a second U-PIT reagent; separating the peptide of interest from the combined first and second protein samples; and determining the relative amount of the first U-PIT reagent and the second U-PIT reagent bound to the peptide or peptides of interest. The U-PIT label of the present inventive methods has the following general formula

A-B-C wherein A is a nucleophilic reactive group, B is a detectable moiety that can be isotopically labeled, and C is a charge replacement group.

20 Claims, No Drawings

MODULAR ISOTOPE CODING APPROACH TO PROTEOMIC ANALYSIS

FIELD OF THE INVENTION

The present invention is directed to focused proteomic analysis for quantitative analysis of a defined subset of a proteomic sample.

BACKGROUND OF THE INVENTION

In the post-genomics era, the trend towards direct analysis of large numbers of proteins in complex biological samples (proteomics) is developing very quickly and becoming a favored method of augmenting, and in some cases replacing, mRNA expression profiling. The traditional approach to proteomics follows these general steps (i) extract proteins from samples, (ii) separate proteins, (iii) enzymatically digest proteins to produce tryptic fragments, (iv) analyze the resulting peptide mixture with mass spectroscopy (MS) or liquid chromatography (LC)/MS or LC/MS/MS to identify mass and, if possible, sequence of peptides, and (v) identify proteins by comparing identified peptides with a database of hypothetically generated digests.

The scope of a comprehensive characterization of all the proteins in a given sample is overwhelming. For the human genome, which contains approximately 35,000 genes, there are 100,000–500,000 potentially expressed gene products (proteins) due to multiple proteins resulting from each gene via alternate gene splicing and post-translational modifications. In general these never all appear in the same sample, so the absolute complexity of realistic proteomics samples maybe reduced to 30–50,000 proteins in a given sample. This, coupled with the fact that protein identification currently depends on the identification of a number of specific and unique proteolytic digest fragments for each protein (approximately 50 peptides per protein in mammals), further complicates the analysis and leads to potentially hundreds of thousands of peptides that need to be separated and analyzed by mass spectrometry. This daunting sample complexity has led to a a number of strategies that are based on reducing the number of analytes which need to be characterized in a given sample by (i) selectively fractionating the sample to a specific subset of interest or (ii) minimizing the number of proteolytically generated peptides required to identify a specific protein.

In genomic analysis of gene expression profiling, the use of DNA microarrays to quantitatively profile transcription of mRNA is used extensively, with mRNA serving as a surrogate for protein expression. Because of the relative chemical and structural homogeneity of nucleic acids, it is much simpler to develop analytical approaches to look at large number of different sequences simultaneously. Additionally, amplification techniques such as PCR allow extremely sensitive detection. This has lead to the availability of DNA microarrays spanning whole genomes. Furthermore, the use of mRNA ignores the complexities introduced by post-translational modifications of proteins, vastly simplifying the number of analytes to be characterized. In some research contexts, the post-translational modifications can be considered extraneous and uninformative. However, the use of mRNA expression profiling has a number of intrinsic disadvantages. Use of mRNA as a surrogate for protein expression disregards lack of correlation between mRNA and protein concentrations, alternative splicing and mRNA modification, protein post-translational modifications and protein degradation.

The conventional approach to proteomics is the separation of all proteins in a given proteome by two dimensional gel electrophoresis (2DGE), spot excision, digestion and identification of the proteins by MS or MS/MS. This approach has advantages in terms of an extremely high separation power, high sensitivity of MS and well-established technological bases. Sufficient research has also been done to validate methods for dealing with a wide range of samples and biological contexts. Two dimensional gel electrophoresis has practical disadvantages because it is relatively slow, labor intensive and shows poor quantitative performance in terms of reproducibility and linearity. Furthermore, the amount of coverage is limited by instrument capabilities and required MS throughput. However, automation and improved instrument design can potentially overcome these problems. Due to imaging sensitivity and loading capacity of the gel media, there is a more fundamental, intrinsic limitation in 2DGE analysis, resulting in a bias towards identification of the most highly expressed proteins. If sufficient total protein sample is loaded onto a gel to allow sufficient representation of the lowest level expressed proteins, the more highly expressed proteins will precipitate in the gel due to overloading or the signal from the high level proteins will be so high that fainter spots are undetectable. This has resulted in a trend towards alternate technologies.

Multidimensional Liquid Chromatography (MDLC) combined with MS should be considered very similar to 2DGE-MS with two significant differences. The separation power of 2DLC is probably not as high as 2DGE, although improvements in technology may improve this situation. More significant is the fact that MDLC does not face the same biasing effect as discussed above for 2DGE. When combined with techniques for isolating specific proteome fractions, MDLC is a very promising approach; however, in the absence of pre-fractionation, MDLC will suffer from problems of dealing with extremely complex samples, which require a large amount of data analysis to extract information relative to a specific research objective.

Aebersold et al. have developed a method called Isotope Coded Affinity Tags (ICAT) in which samples are derivatized with a cysteine specific reagent which contain a heavy/light form. See, e.g., Gygi et al., Nat. Biotech., 17 (10): 994–99 (1999); PCT Publication No. WO 00/11208 (Aug. 25, 1999); see also U.S. Pat. No. 5,721,099 (Jun. 7, 1995). In ICAT, after tagging, the samples are pooled, proteolytically digested and then the tagged fragments are isolated by a biotin/streptavidin affinity interaction using a biotin functionality that is also part of the ICAT reagent. The resulting peptides are analyzed by LC-MS or matrix assisted laser desorption ionization time-of-flight mass spectrometry (MALDI-TOFMS) and the relative quantitative expression levels of the two samples can be determined by ratioing the abundance of the heavy and light forms of each peptide. This approach has generated a great deal of interest in the research community and has a number of potential advantages compared to the brute force methods described above. Specifically, the approach leads to a significant simplification of the proteome by only requiring the analysis of cysteine containing peptides. The method also allows accurate relative quantitative characterization by using a control sample as the internal standard for every peptide.

However, ICAT method makes a number of assumptions that may or may not be justified. The first assumption is that every protein includes a cysteine that can be derivatized. In *S. cerevisiae*, for example, based on genomic sequences, 8% of the proteins do not contain cysteine residues. A second limitation is that information about a single peptide (mass and partial sequence information) is sufficient to identify a protein by comparison with a database. There are some practical limitations as well. Users have reported problems and/or dissatisfaction in the reproducibility, linearity, cost and ease of use with the ICAT approach. Moreover, the ICAT approach does not introducing any selectivity with respect to targeted analysis. Although the technique simplifies the proteome, it does so based on the basis of selecting only peptides with a specific residue rather than a specific characteristic of interest, such as function. Another potential disadvantage of the ICAT approach is that the coupling of the Isotope Coding with the Affinity Tagging limits the flexibility of this technology to adapt to new applications.

Smith et al. have developed a similar technique termed Phosphoprotein Isotope Coded Affinity Tag (PhIAT). See Goshe et al., *Anal. Chem.*, 73: 2578–86 (2001); see also Weckwerth et al., *Rapid Commun. Mass Spectrom.* 14: 1677–81 (2000). Briefly, PhIAT is a second cousin to the ICAT cysteine labeling reagent, differing from ICAT in that PhIAT is designed to enrich and quantify differences in the O-phosphorylation states of proteins.

Phosphorylation is a major protein post-translational modification, which is involved in the modulation of protein activity and propagation of signals within cellular pathways and networks. Serine, threonine and tyrosine are the hydroxylamino acids that can typically undergo phosphorylation. Lysine, arginine and cysteine can also be phosphorylation but to a much smaller degree. PhIAT does not currently work for tyrosyl phosphorylation. Although 99% of the phosphorylated peptides from the Yeast proteome are serine or threonine modified residues, this does not diminish the importance of tyrosine phosphorylation. As such, it is important to expand PhIAT to include tyrosyl phosphorylation.

A more general approach to expression proteomics has been described by Fenselau et al. in which two $^{18}O$ labels are introduced universally into the carboxyl termini of each peptide by carrying out proteolytic digestion in $^{18}O$ enriched water. See Yao et al., *Anal. Chem.*, 73: 2836–42 (2001). In a similar manner to ICAT and PhIAT, the resulting peptides are quantitated by comparison with a control sample digested in normal water. The "heavy" sample will show a 4 amu mass shift over the "light sample." This is a very attractive and simple approach. Initially, the only major disadvantage compared to the current proposed invention is that a mass difference of >4amu is desirable to avoid interferences with the natural isotope distribution and resolution issues of the doubly charged peptide.

Regnier et al. described an approach termed "Signature Peptides." See Geng, *J Chrom. A.*, 870: 295–313 (2000); see also U.S. Publication No. U.S. 2002/0037532 A1 (Mar. 28, 2002). The main focus of this was not labeling, though there was mention of acylating primary amino groups with N-acetoxysuccinamide. The "heavy" tag introduced in this case resulted only a 3 amu mass shift. In the description of this approach, it appeared that there was application of this internal standard labeling only to a small subset of peptides; however, how these were selected was not clear. In this approach, peptides that contain only a C-Terminal lysine lost all positive charge and, consequently, had to be analyzed in negative ion mode mass spectrometry (in this case by MALDI-TOFMS). Lack of positive charge would also have some effects on the chromatographic separation characteristics.

BRIEF SUMMARY OF THE INVENTION

The present invention provides methods for analyzing a peptide or peptides of interest in a protein sample comprising providing a first protein sample and a second protein sample; labeling the first protein sample with a first Universal Peptide Isotope Tag (U-PIT) reagent and the second protein sample with a second U-PIT reagent; separating the peptide or peptides of interest from the combined first and second protein samples; and determining the relative amount of the first U-PIT reagent and the second U-PIT reagent bound to the peptide or peptides of interest. The U-PIT label of the present inventive methods has the following general formula

wherein A is a nucleophilic reactive group, B is a detectable moiety that can be isotopically labeled, and C is a charge replacement group.

DETAILED DESCRIPTION OF THE INVENTION

The present invention relates to focused proteomic analysis, which involves quantitative analysis of a carefully defined subset of a proteomics sample. A novel aspect of this invention is the combination of a relatively generic isotope tag with a decoupled selection process, allowing simplified customization of the application with a single reagent.

The present invention follows these general steps: (a) providing a first protein sample and a second protein sample; (b) labeling the first protein sample with a first U-PIT reagent and the second protein sample with a second U-PIT reagent, which reagent can be such that for one protein sample the reagent is an isotopically heavy form (e.g., 8 deuteriums) and for the other protein sample, the reagent is an isotopically light form; (c) separating the peptide or peptides of interest from the combined first and second protein samples, such as by affinity chromatography, for example; (d) and determining the relative amount of the first U-PIT reagent and the second U-PIT reagent bound to the peptide or peptides of interest by, for example, determining the mass and sequence of the remaining peptides, which can be done using, for example, LC/MS/MS. The peptide of interest can optionally be identified and/or quantitated based on the relative signals of the isotopically heavy and light forms for a given peptide. It should be appreciated that the order of the method steps set forth herein is simply a preferred order and not required. Accordingly, the first and second protein samples can be labeled subsequent to either combination of the first and second protein samples or separation of the peptide or peptides of interest from the combined first and second protein samples.

The success of this approach is based on the fact that most biological studies do not require the analysis of all proteins in a sample to answer the biological question under examination. Rather, there is a subset that can be defined by functional or structural similarities that are most important. The functional and/or structural similarities are the basis for the physical isolation of the peptides of interest, for which functional or structural features are invariant under proteolytic digestion. Success of this approach is also based on the fact that a small number of peptides are sufficient to unequivocally identify a protein. The peptides of interest in the present invention, when labeled with heavy or light isotopes, behave in a sufficiently similar way to allow relative quantification by comparison of mass spectrometric intensities. The methods of the present invention can be used to analyze phosphorylated proteins, glycosylated proteins, transcription factor proteins, membrane proteins, proteins involved in protein-protein interactions, and post translationally modified proteins (e.g., ubiquitinated proteins) and to remove high level background proteins. Specific methods for analyzing these types of protein samples are described in detail below.

The protein samples of the present invention, which can be isolated from any suitable source, including humans, preferably contain a plurality of peptides, polypeptides, or proteins (i.e., a complex mixture of peptides, polypeptides, or proteins). Preferably, there are at least about 100 peptides, polypeptides, or proteins, more preferably at least about 1000 peptides, polypeptides, or proteins. It should be appreciated that the protein samples can contain several thousand proteins or polypeptides. However, when a complex mixture containing thousands of proteins is fragmented, it is probable that a hundred thousand or more polypeptides or peptides will be generated. The protein samples of the present invention preferably contain a peptide or peptides of interest. Also preferably, the first protein sample and a second protein sample are equivalent in that they contain a similar mixture of proteins.

It should be appreciated that the terms peptide, polypeptide, and protein are used herein interchangeably to refer to a polymer of amino acids and do not connote a specific length of a polymer of amino acids. Thus, for example, the terms oligopeptide, polypeptide, and enzyme are included within the present inventive methods. In addition, the peptides, polypeptides, and/or proteins of the present invention can be produced using recombinant techniques, chemical or enzymatic synthesis, or naturally occurring. These terms also include peptides, polypeptides, and/or proteins that have been modified or derivatized, such as by glycosylation, acetylation, phosphorylation, ubiquitination, and the like.

Prior to labeling the first protein sample with a first U-PIT reagent and the second protein sample with a second U-PIT reagent, the first protein sample and the second protein sample can be fragmented. It should be appreciated that the order of the method steps set forth herein is simply a preferred order and not intended to be required. Therefore, fragmentation of the proteins can occur prior to combination of the first and second protein samples (as discussed below) or separation of the peptide or peptides or interest from the combined first and second proteins samples.

Fragmentation or cleavage can be achieved using any suitable method, such as by chemical, enzymatic, or physical means. Suitable chemical means, for example, includes fragmentation using pharmic acid or CmBr. Examples of suitable enzymatic methods include proteolytic cleavage (such as tryptic cleavage). Preferably, endoproteinase Lys C, which selectively cleaves at the —COOH side of lysine, can be used to proteolytically digest peptides to consistently produce peptides with two sites available for tagging. Factor XA or Sumaxillaris Protease, which selectively cleave only the —COOH side of arginine, also preferably can be used to proteolytically digest peptides to produce fragments that would accept only a single tag. It should be understood that in the context of the present invention, cleavage, proteolytic cleavage, proteolysis, fragmentation, and the like are used interchangeably and refer to scission of a chemical bond within peptides or proteins to produce peptide or protein fragments or cleavage fragments.

When the proteins are fragmented by proteolytic cleavage, the proteins are preferably alkylated with an alkylating agent prior to the proteolytic cleavage. This is in order to prevent the formation of dimers or other adducts through disulfide/dithiol exchange. Optionally, the proteins can be reduced prior to fragmentation or alkylation in order to facilitate the alkylation reaction and subsequent fragmentation. Some proteins are resistant to proteolysis unless they have been reduced and alkylated prior to cleavage.

In addition, prior to labeling the first protein sample with a first U-PIT reagent and the second protein sample with a second U-PIT reagent, the first protein sample and the second protein sample can be combined. It should be appreciated that the order of the method steps set forth herein is simply a preferred order and not intended to be required. Therefore, combination of the first and second protein samples can occur prior to fragmentation or separation of the peptide or peptides or interest from the combined first and second proteins samples.

For simplicity, reagents or tags useful in the context of the present inventive methods are referred to herein as Universal Peptide Isotope Tags (U-PITs). The first protein sample is labeled with a first U-PIT reagent and the second protein sample with a second U-PIT reagent. U-PIT reagents are generic in the sense that they can react with all or nearly all members of a particular class of proteins. A U-PIT has the following formula

A-B-C wherein A is a nucleophilic reactive group, B is a detectable moiety that can be isotopically labeled, and C is a charge replacement group. The U-PIT described herein is useful and unique when used in conjunction with the present inventive methods of isolating a specific subset of the proteome, thus simplifying the analytical problem and targeting the data generation and analysis towards a specific goal.

In the context of the present inventive methods, a U-PIT will react at least once, and preferably only once, with every fragmented peptide in the sample. In one embodiment, a U-PIT reacts with one or more side chains of amino acids with high abundance. The reagents of the present invention can react with the N-terminus of the peptide, the C-terminus of the peptide, or the amino acid side chain of the C-terminus amino acid, such as lysine, for example.

In one preferred embodiment, a U-PIT reacts with the N-terminal amino group or the amino side chain of the C-terminal amino acid. For example, if a reagent reacts with primary amines and if the tryptic cleavage site is an arginine, the reagent will attach once to the C-terminal primary α-amine and not with the secondary amines on the basic side chain of the C-terminal amino acid. However, if the tryptic cleavage site is lysine, the reagent will react once with the primary α-amine and a second time with the primary amine on the side chain.

A U-PIT has various other characteristics. For example, a U-PIT preferably maintains the charge state of the peptide. Thus if the charge of a primary amine is removed by the reaction, it should be replaced by a single charge on the reagent itself. The reagent also preferably does not affect the separation characteristics of the peptide; in general, this will favor small, hydrophilic tags. The U-PIT can additionally be designed to incorporate a detectable label. The label for detection can be an enzyme, a radioactive isotope or a fluorophore.

Furthermore, a U-PIT preferably incorporates at least an 8 amu mass difference between the heavy and light forms, resulting in a sufficiently high mass difference to allow straightforward identification of the two forms of a doubly or triple charged peptide with a typical ion-trap resolution, while minimizing differential retention effects caused by a large difference. Therefore, the present inventive methods are preferably carried out using a first U-PIT reagent and a second U-PIT reagent that are chemically equivalent and isotopically different.

A reagent preferably reacts with the target peptide rapidly and at room temperature in aqueous media, quantitatively yielding a single product with no by-products or side reactions and requiring minimal cleanup. Also preferably, a reagent reaction is not sensitive to the presence of sample-matrix materials, such as salts, nucleic acids, small molecules, etc. A U-PIT is preferably non-toxic and water-soluble, as well as the reaction chemistry taking place in an aqueous system. Additionally, a reagent is inexpensive to produce and stable for shipping and storage, and when bound to the target peptide.

Moreover, various preferred characteristics of a U-PIT allow for identification and quantitation of the peptide of interest. For example, identification of the peptide of interest is simplified if, under conditions of collisionally induced dissociation, the attachment of the U-PIT tag to the peptide is stronger than the peptide bonds in the peptide of interest, which results in a consistent mass shift of the N-terminal fragment. Also, a reagent preferably has an efficient chromophore or fluorophore, which can be used for quantitation of the peptide of interest.

In one aspect, the U-PIT reagent comprises a nucleophilic reactive group (A). The nucleophilic reactive group is capable of reacting with a nucleophile that may be present on the peptide. The nucleophile on the peptide may be N, S or 0, such as a primary or secondary amine of an amino acid, or the carboxylate or phenolate of an amino acid of the peptide. The nucleophilic reactive group can thus normally be a leaving group that can be selected based on a particular nucleophilic group on the peptide to be tagged.

When the nucleophile is an amine, the nucleophilic reactive group can include a reactive carbonyl or carbonyl equivalent, and a leaving group which may be displaced in a nucleophilic displacement reaction by the amine. "Carbonyl or carbonyl equivalent" includes, without limitation, carboxylic acids, esters, amides, anhydrides, acyl halides, and isocyantes. "Leaving group" means a moiety capable of nucleophilic displacement by an amine, e.g., —NH$_2$. Any leaving group can be used here provided it is readily removed by nucleophilic displacement. Non-limiting examples of leaving groups useful in the invention include halo, such as bromo, chloro, iodo, 0-tosyl, 0-triflyl, 0-mesyl and the like. In addition, the leaving groups useful in the invention include sucinimide, maleimide, glutarimide, isatin and phthalimide.

In one preferred embodiment of a U-PIT, (A) has the following formula

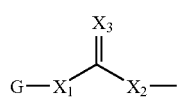

wherein G is selected from group consisting of succinimide, maleimidie, glutarimide, isatin, phthalimide and halo-acetone; $X_1$ and $X_3$ are independently selected from group consisting of $CR_1R_2$, S, and $NR_3$, wherein $R_1$, $R_2$, and $R_3$ are independently hydrogen or a lower alkyl; and $X_2$ is a direct bond or is selected from the group consisting of $CR_1R_2$, S, and $NR_3$, wherein $R_1$, $R_2$, and $R_3$ are independently hydrogen or a lower alkyl. Preferably, A comprises

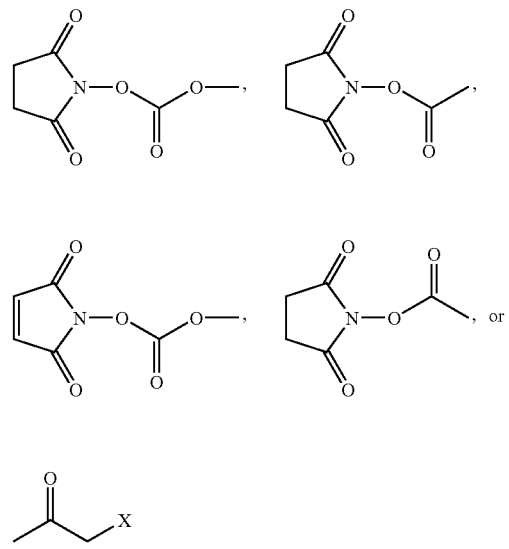

wherein X is a halogen selected from the group consisting of Cl, Br, and I.

Additionally, the U-PIT can comprise a detectable moiety, such as a moiety capable of being isotopically labeled, for example. The detectable moiety can be, for example, a label for detection by an enzyme, a radioactive isotope, a heavier isotope, or a fluorophore, preferably a heavier or lighter isotope. In one aspect, all the atoms in a selected region, comprising (B) or the detectable moiety, of the U-PIT reagent can be isotopically labeled. In another aspect, only one atom of B can be isotopically labeled, preferably between 2–15 atoms are isotopically labeled, more preferably between 2–9 atoms are isotopically labeled, and integers in between, such as, for example, 3, 4, 5, 6, 7, and 8.

A U-PIT is isotopically labeled such that the mass difference between the labeled and unlabeled regent is sufficiently high to allow for identification of the two forms of a doubly or triple charged peptide with a typical ion-trap resolution. However, the mass difference preferably is not so high that it causes differential retention effects for the peptides. Thus, the reagent preferably incorporates at least about 8 amu mass difference between the heavy and the light forms, preferably about 8 amu to about 100 amu mass difference, more preferably about 8 amu to about 50 amu mass difference, or most preferably about 8 amu to about 20 amu mass difference, or any integer between the stated ranges.

The preferred isotope can be selected from $^2H$, $^3H$, $^{13}C$, $^{14}C$, $^{32}P$, $^{34}S$, $^{35}S$, $^{36}Cl$, $^{37}Cl$, $^{18}O$, $^{15}N$, $^{81}Br$, $^{123}I$, $^{125}I$ and $^{131}I$, and combinations thereof. In one aspect, the region of U-PIT that comprises the detectable moiety is an isotopically tagged group (B), and includes substituted 1,3,5-triazine having the structure below:

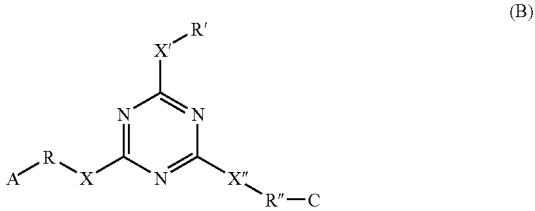

where A is the nucleophilic reactive group, C is the charge replacement group, X' and R' taken together can be H, $^2$H, $^3$H, $^{36}$Cl, or $^{37}$Cl. In addition, X, X' and X" can be independently selected to be NH, O, or S, and R, R' and R" can be independently selected to be hydrogen, alkyl, alkenyl, alkynyl, aryl, heteroaryl, or $(CZ_2CZ_2O)_n$ where Z=H, $_2$H, $^3$H, and n is an integer between 1 and 15, preferably between 1 and 5. As will be evident to one of skill in the art, the natural atoms comprising the isotopically tagged group (B) of the U-PIT reagent can be replaced with varying numbers of $^2$H, $^{13}$C, $^{37}$Cl, or $^{15}$N, for example.

C can be a quaternary nitrogen derivative, which can comprise the following formula

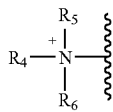

wherein $R_4$, $R_5$, and $R_6$ are independently selected from the group consisting of hydrogen, lower alkyl and aryl.

In another aspect of the invention, the isotopically tagged group of the U-PIT reagent comprises substituted or unsubstituted 1,2,4-triazine or 1,2,3-triazine, where the substituents are as described above. As will be evident to one of skill in the art, the triazine structure can be replaced with an aryl group, such as benzene, a heteroaryl group, such as pyridine, imidazole, pyrrole, or thiophene, or an alkyl group, such as ethyl, propyl, isoproyl, butyl, tert-butyl, polyethyleneglycol, and the like.

In another aspect, the isotopically tagged group additionally includes a detectable label such as a fluorophore, a radioactive isotope or an enzyme label. A number of fluorescent materials are known and can be utilized as labels. These include, for example, fluorescein, rhodamine, auramine, Texas Red, AMCA blue and Lucifer Yellow. Exemplary fluorescent dyes for use with the invention include water-soluble rhodamine dyes, fluoresceins, 4,7-dichlorofluoresceins, benzoxanthene dyes, and energy transfer dyes. Further specific exemplary fluorescent dyes include 5- and 6-carboxyrhodamine 6G; 5- and 6-carboxy-X-rhodamine, 5- and 6-carboxytetramethylrhodamine, 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8-dibenzo-4',5'-dichloro-5- and 6-carboxy-4,7-dichlorofluorescein, 2',7'-dichloro5- and 6-carboxy-4,7-dichlorofluorescein, and 2',4',5',7'-tetrachloro-5- and 6-carboxy-4,7-dichlorofluorescein. Most preferably, the dye is a fluorescein or a fluorescein derivative.

The U-PIT reagent can also be labeled with a radioactive element or with an enzyme. The radioactive label can be detected by any of the currently available counting procedures. Enzyme labels are likewise useful, and can be detected by any of the presently utilized calorimetric, spectrophotometric, fluorospectrophotometric, amperometric or gasometric techniques. The enzyme can be conjugated to the U-PIT reagent by reaction with bridging molecules such as carboduimides, diisocyanates, glutaraldehyde and the like. Many enzymes that can be used in these procedures are known. The preferred peroxidases are β-glucuronidase, β-D-glucosidase, β-D-galactosidase, urease, glucose oxidase plus peroxidase and alkaline phosphatase. In another aspect, the isotopic tagged group additionally includes an affinity label. The affinity label can be biotin, digoxin, fluorescein, dinitrophenol, and the like, that can bind to avidin, antibody for digoxin, antibody for fluorescein, and antibody for dinitrophenol, respectively.

In one aspect of the invention, the U-PIT reagent comprises a charge replacement group (C). The charge replacement group can be selected based on ease of synthesis, increase in ionization efficiency of labeled peptides, and formation from a labeled peptide of a specific fragment ion series with minimal unfavorable label fragmentation. The charge replacement group includes compounds of the quaternary nitrogen derivatives, quarternary phosphonium derivatives, substituted pyridinium derivatives and sulfonium derivatives. Preferred charge replacement groups are dimethylalkylammonium derivatives and substituted or unsubstituted pyridinium derivatives.

The charge replacement components include, but are not limited to, primary, secondary, or tertiary alkyl or aryl ammonium groups, substituted and unsubstituted heterocyclyl and heteroaryl (e.g., pyridinium) groups, alkyl or aryl Schiff base or imine groups, and guanidino groups. In one aspect of the invention, the charge replacement moiety of the U-PIF reagent includes tetraalkyl or tetraaryl ammonium groups, tetraalkyl or tetraaryl phosphonium groups, and N-alkylated or N-acylated heterocyclyl and heteroaryl (e.g., pyridinium) groups. The quaternary nitrogen derivative can be $R_1R_2R_3N^+$—where $R_1$, $R_2$, and $R_3$ are independently selected to be H, lower alkyl, alkene, or aryl. For example, $R_1$, $R_2$, and $R_3$ can be H, methyl, propyl, isopropyl, butyl, tert-butyl, and the like.

The charge replacement group, as will be understood by one of ordinary skill in the art, will be accompanied by counter ions of opposite charge. For example, the counter ions for positively charged groups include oxyanions of lower alkyl organic acids (e.g., acetate), halogenated organic acids (e.g., trifluoroacetate), organosulfonates (e.g., N-morpholinoethane sulfonate), as well as $Cl^-$, $Br^-$, $HSO_4^-$, $BF_4^-$ and $ClO_4^-$.

One preferred U-PIT has the following formula (I)

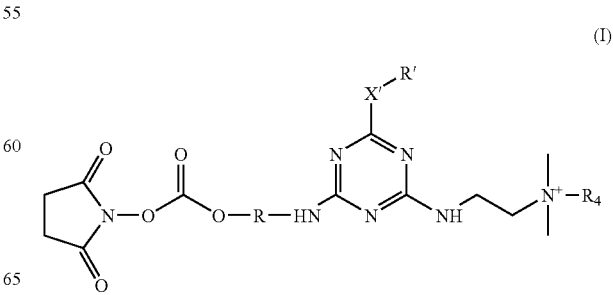

wherein X' and R', taken together, are H or a halogen; X' is NH, O, or S; R and R' are independently selected from the group consisting hydrogen, an alkyl, an alkenyl, an aryl, a heteroaryl, and $(CH_2CH_2O)_n$, wherein n is an integer between 1 and 5; and $R_4$ is selected from the group consisting of hydrogen, a lower alkyl, and an aryl. In some of the compounds, X', R' and/or R are isotopically labeled.

Another preferred U-PIT has the following formula (II)

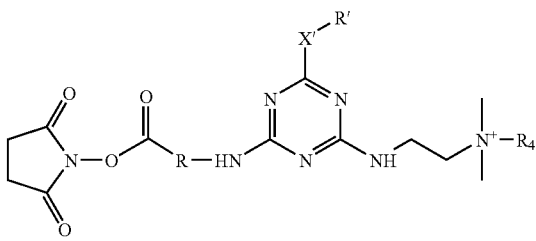

(II)

wherein X' and R', taken together, are H or a halogen; X' is NH, O, or S; R and R' are independently selected from the group consisting hydrogen, an alkyl, an alkenyl, an alkynyl, an aryl, a heteroaryl, and $(CH_2CH_2O)_n$, wherein n is an integer between 1 and 5; and $R_4$ is selected from the group consisting of hydrogen, a lower alkyl, and an aryl. In some of the compounds, X', R' and/or R are isotopically labeled.

Another preferred U-PIT has the following formula (III)

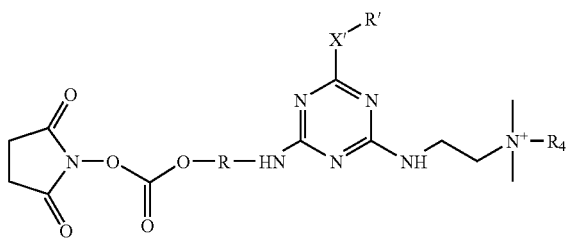

(III)

wherein X' and R' taken together are H or halogen; X' is NH, O, or S; R and R' are independently selected from the group consisting hydrogen, alkyl, alkenyl, alkynyl, aryl, heteroaryl, and $(CH_2CH_2O)_n$ where n is an integer between 1 and 5; and $R_4$ is selected from the group consisting of hydrogen, lower alkyl and aryl.

Yet another preferred U-PIT has of the following formula (IV)

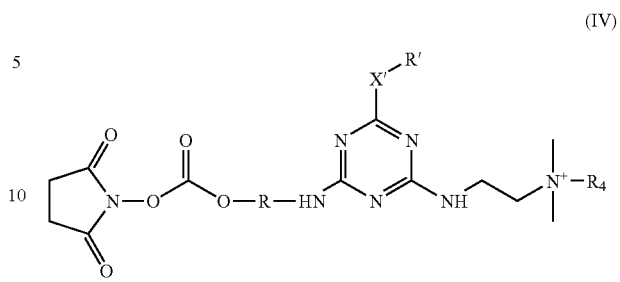

(IV)

where X' and R' taken together are H or halogen; X' is NH, O, or S; R and R' are independently selected from the group consisting hydrogen, alkyl, alkenyl, alkynyl, aryl, heteroaryl, and $(CH_2CH_2O)_n$ where n is an integer between 1 and 5; and $R_4$ is selected from the group consisting of hydrogen, lower alkyl and aryl.

Still another preferred U-PIT reagent has the following formula (V) or (VI)

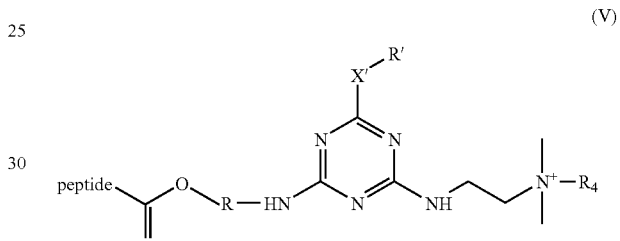

(V)

or

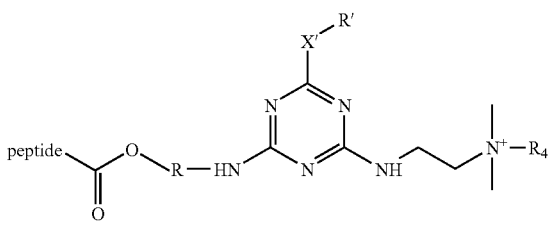

(VI)

where X' and R' taken together are H or halogen; X' is NH, O, or S; R and R' are independently selected from the group consisting hydrogen, alkyl, alkenyl, alkynyl, aryl, heteroaryl, and $(CH_2CH_2O)_n$ where n is an integer between 1 and 5; and $R_4$ is selected from the group consisting of hydrogen, lower alkyl and aryl.

A more particularly preferred U-PIT has the following formula (VII)

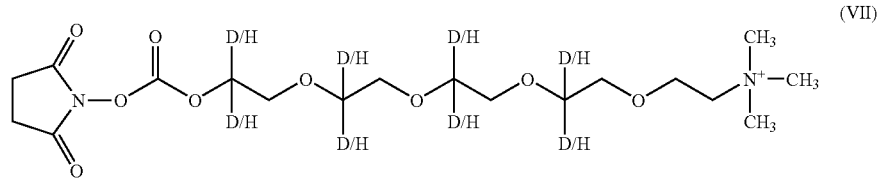

(VII)

such that compound in formula III can be isotopically labeled with deuterium (D) at any or all of the positions.

The U-PIT reagents comprise the nucleophilic reactive group (A), the isotopically labeled group (B), and the charge replacement group (C), as described above. The compounds of the present invention, having the structure A-B-C, can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 3$^{rd}$ Ed., Vols. A and B (Plenum 1992), and Green and Wuts, PROTECTIVE GROUPS IN ORGANIC SYNTHESIS 2$^{nd}$ Ed. (Wiley 1991). Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England) and Trans World Chemicals (Rockville, Md.).

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts. U-PIT reagents can be synthesized using the following general procedures of Examples 1–4. The isotopically labeled U-PIT reagent can be prepared by either using isotopically labeled starting material or by making the unlabeled compounds and then isotopically labeling them by methods well known in the art.

Once the first and second protein samples are labeled with a first and second U-PIT, respectively, the first and second protein samples are combined. Following combination, the peptide of interest is separated or fractionated from the combined first and second protein samples. The methods of the present invention are not limited by the techniques used for selection and/or fractionation and any suitable method can be used. Typically, separation is carried out using single or multidimensional chromatography such as reversed phase chromatography (RPC), ion exchange chromatography, hydrophobic interaction chromatography, size exclusion chromatography, bead separation, spin-column separation, immunoprecipitation, or affinity fractionation such as immunoaffinity and immobilized metal affinity chromatography, or a combination thereof. For example, electrophoresis, either slab gel or capillary electrophoresis, can also be used to fractionate the peptides; examples of slab gel electrophoretic methods include sodium dodecyl sulfate polyacrylamide gel electrophoresis (SDS-PAGE) and native gel electrophoresis. Capillary electrophoresis methods that can be used for fractionation include capillary gel electrophoresis (CGE), capillary zone electrophoresis (CZE) and capillary electrochromatography (CEC), capillary isoelectric focusing, immobilized metal affinity chromatography and affinity electrophoresis. Other affinity separation methods can be used for particular applications, examples of which are described in detail below.

Once the peptide of interest is separated, it is then analyzed. Any suitable method can be used to analyze the peptide of interest. Masses of the peptides of interest can be determined by liquid chromatography, mass spectrometry, preferably using matrix assisted laser desorption ionization (MALDI) or electrospray ionization (ESI), and mass of the peptides can be analyzed using time-of-flight (TOF), quadrapole, ion trap, magnetic sector or ion cyclotron resonance mass analyzers, or a combination thereof (e.g., LC/MS, LC/MS/MS, MALFI-TOFMS, or TOF/TOF). See, e.g., Perkins et al., *Electrophoresis,* 20(18): 3551–3567 (1999); Bairoch, Proteome databases, (In) Proteome research: new frontiers in functional genomics, Wilkins et al., Eds., 93–132, Springer Verlag, Heidelberg, (1997). Preferably the mass of the peptides is determined with a mass accuracy of about 10 ppm or better; more preferably, masses are determined with a mass accuracy of about 5 ppm or better; most preferably they are determined with a mass accuracy of about 1 ppm or better. The lower the ppm value, the more accurate the mass determination and the less sequence data is needed for peptide identification.

The peptide of interest can further be identified and/or quantited. In the descriptions below, the focus is on the specific fractionation or isolation method for the class of proteins of interest. However, it has to be emphasized that the ability to quantitate these proteins can be enabled by the combination of the U-PIT labeling procedure and the specific isolation method, such that the combined analytical power should be viewed as more than the sum of their individual isolated utility.

The present invention also provides a computer system for analyzing the peptides of interest comprising (a) a database including records comprising protein modifications data; (b) one or more algorithms for statistically analyzing the protein modifications data; (c) one or more algorithms for coordinating the statistically analyzed protein modifications data; (d) a system for output and presentation of the results from the algorithms; (e) a repository systems to index and stored the database and results; and (f) a query system for retrieval of database and results. Such a computer system can further comprise (a) a database including records of known protein modifications data; (b) one or more algorithms for comparing the protein modifications data with the known protein modifications data to generate comparison data; (b) one or more algorithms for coordinating the comparison data; (d) a system for output and presentation of the results from the algorithms; (e) a repository systems to index and stored the database and results; and (f) a query system for retrieval of database and results.

Alternatively, the computer system can further comprise (a) a database including records comprising quantities of the modified proteins; (b) a database including records comprising known protein quantity data; (c) one or more algorithms for comparing the quantities of the modified protein with the known protein to generate comparison data; (d) one or more algorithms for coordinating the comparison data; (e) a system for output and presentation of the results from the algorithms; (f) a repository systems to index and stored the database and results; and (g) a query system for retrieval of database and results. A computer-readable storage medium comprising digitally encoded data, wherein the data comprise protein modifications generated according to the present inventive methods is also provided.

The methods of the present invention will vary depending on the requirements of the biological questions that are being asked. A feature of this approach is that the isotope tagging and the affinity selection have been decoupled allowing independent optimization of both features. Not only will this allow potentially better performance from each module, it will also allow rapid development of a suite of different focused solutions in which the isotope tagging is constant and the affinity selection is customized and adapted for each new problem. In one embodiment, proteins can initially be proteolytically digested and then isolated. In a second embodiment, proteins must be isolated intact. In general, this embodiment has applications where the tertiary structure of the protein is the characteristic factor; for example, in application investigating high level proteins, protein-protein interactions, membrane proteins, and transcription factors.

The general approach can be grouped into a number of categories, depending on the requirements of the specific chemistries needed to isolated the fraction of interest. For approaches in which the proteins must be isolated intact, the methods of the present invention can involve the following general steps, for example (samples are treated separately for steps a–f and treated as a single pool for steps g–k): (a) initial sample preparation, which can involve protein isolation or filtering; (b) isolate fractions of interest by affinity separation; (c) denature; (d) reduction/alkylation, which may not be needed in all cases; (e) proteolytic digestion; (f) label with U-PIT reagent; (g) Pool Samples; (h) Analyze by LC/MS. LC/MS/MS, LC/LC/MS/MS or MALDI-MS; (i) data processing (generic MS Chromatographic and Spectral Manipulation, Database Search); (j) data processing (Customized Quantitative Expression Analysis); (k) data processing (Customized Interpretive Software, the requirements of which depend on application). For approaches in which the proteins can be isolated after digestion, which includes applications where a specific chemical moiety is the characteristic factor, such as, for example, phosphorylation, ubiquitination, disulfide bond formation, glycosylation, etc., the methods of the present invention involve the following general steps (samples are treated separately for steps a–e and treated as a single pool for steps f–k): (a) initial sample preparations, which can involve protein isolation or filtering; (b) denature; (c) reduction/alkylation, which may not be necessary or appropriate for all applications, e.g. disulfide bond analysis; (d) proteolytic digestion; (e) label with U-PIT reagent (f) pool samples; (g) isolate fraction of interest by affinity separation; (h) analyze by LC/JMS, LC/MS/MS, LC/LC/MS/MS or MALDI-TOFMS; (i) data processing (generic MS chromatographic and spectral manipulation, database search); (j) data processing (Customized Quantitative Expression Analysis); (k) data processing (Customized Interpretive Software, requirements of which depend on application).

In most of the applications described below, the affinity selection and isolation of a specific subset of the proteome is the key feature. The uniqueness of the present inventive methods lies in the specific interaction that the affinity method is based on when taken with the U-PIT labeling methodology. In several cases, for example, transcription factors and membrane proteins, the interaction itself may also be novel. It should be appreciated that the format of the affinity separation can take a number of forms including, but not limited, chromatographic methods, bead-based methods, spin-column-based methods or immunoprecipitation-like methods. For purposes of the present invention, the proteins can be analyzed by any suitable method. The complexity of the labeled peptide mixture after the affinity isolation step will dictate the analytical demands on the separation technique. A preferred method of analysis is multidimensional LC-MS/MS; however, simpler separation techniques or the use of MALDI-TOFMS could also be used.

The present inventive methods can be used to analyze protein phosphorylation, which is one of the most common and important protein post-translational modifications. This reversible covalent modification is involved in signal transduction, cell division and cancer. Esterification of an amino acid side chain by the addition of phosphate causes conformational changes in the protein and consequently altered protein activity or stability. Of prime interest is the role that phosphorylation plays in signaling pathways through transduction of extracellular signals and coordination of intracellular events. Although the importance of this process is well recognized, only a subset of phosphoproteins is known and their inter-relationships are not fully understood.

Protein phosphorylation is catalyzed by a class of enzymes referred to as kinases, while the removal of phosphates is catalyzed by a group of enzymes called phosphatases. The typical acceptors in eukaryotic systems are serine, threonine and tyrosine, while bacteria favor histidine, aspartic acid and glutamic acid. Although serine and threonine phosphorylation is more common than tryosine phosphorylation (in approximate abundance ratios of 1000/100/1 serine/threonine/tyrosine), this does not reflect the profound importance of tyrosine due to its involvement in transmembrane tyrosine kinase pathways. In eukaryotic systems, these enzymes are generally separated into two classes: serine/threonine specific and tyrosine specific.

Accordingly, the present inventive methods can be used to delve into various areas of inquiry in the area of protein phosphorylation. For example, these methods can be used to determine, within a given proteome, which proteins are phosphorylated and the specific sites of phosphorylation. These methods can also be used to determine the relative quantitative relationships of specific phosphoproteins between two proteomic samples. Within a single proteome, these methods can additionally be used to determine the relative quantitative relationships of phosphorylated and dephosphorylated states of specific proteins, as well as the relationships of specific phosphoproteins in pathways and cascades and the dynamic behavior of such a cascade. Each of these different areas of inquiry will require slight modifications to the analytical procedure as well as the post-analysis data processing, which modifications can easily be made by one of skill in the art.

For analysis of protein phosphorylation, the U-PIT reagent can be used in combination with a specific reagent for isolation of the phosphorylated peptides that result from the proteolytic digest of the proteomic samples. Various suitable affinity methods can be used. Immobilized Metal Affinity Chromatography (IMAC), for example, is a preferred well-established technique that has been used in the past for the isolation of phosphoproteins. In the past, IMAC has been limited due to steric effects; however, since the present inventive methods involve isolation of phosphopeptides, steric hindrance should not be a problem. There have also been improvements in IMAC performance (Ficarro et al., *Nat. Biotechnol.*, 20(3): 301–5 (2002)). Another approach is the use of affinity chromatography based on either natural antibodies or synthetic antibody mimics. Again, these approaches are known in the art to work with both phosphoproteins and phosphopeptides and would be ideal as a simple approach for isolating the previously labeled peptides.

For the comparison of expression levels of phosphoproteins between two different proteomic samples, the following methods can be used. Each sample is denatured, reduced and alkylated, followed by tryptic digestion. Following digestion, the peptides are labeled with an isotope coded NHS-ester based reagent. One sample should be labeled with the heavy (D8 or $^{14}$C8), while the other is labeled with the light reagent (D0 or $^{14}$C0), labeling the N-terminal amine, the C terminal lysine side chain and any internal lysines that remain due to incomplete cleavage. The reagent should be constructed such that the positive charge states of the peptides are maintained. Although this reagent need not include an affinity capture moiety, in principle, the reagent used can be the standard ICAT reagent, with the addition of the use of Avidin/Biotin affinity purification.

Once the samples are labeled, they are pooled and the phosphopeptides isolated by affinity or IMAC based separations technology followed by 1- or 2-D HPLC-MS/MS analysis. Decoupling labeling and affinity capture may reduce the specificity, which makes this approach applicable to a wide range of problems by adapting the specific isolation step to fit the problem. The ratios of Heavy to Light Tags for a given peptide (and consequently protein) will reflect the relative degree of phosphorylation of that protein in each sample. MS/MS also can be done to determine the specific phosphorylation site.

For quantitation of fractional phosphorylation of different proteins in a single proteome, the following procedure could be used. For the entire sample, the proteome is reduced, alkylated and digested. Following this, the phosphorylated peptides are captured by IMAC or Affinity chromatography (Fraction B). For the rest of the non-phosphorylated peptides, all the peptides that are susceptible are enzymatically phosphorylated. The in vitro phosphorylated peptides are then captured by IMAC or Affinity Chromatography (Fraction B—ALSO FRACTION B?). Fraction A is labeled with the Heavy Reagent described above and Fraction B is labeled with the Light Reagent described above. The labeled fractions are then pooled.

Once the samples are pooled, the samples are analyzed by multidimensional HPLC-MS/MS. As an option, if added specificity is needed, the phosphopeptides can be further isolated before LC/MS analysis using a second (different) phosphopeptide specific capture step (IMAC or affinity). The ratios of Heavy to Light reagent for each peptide will reflect the degree to which that peptide, and consequently protein, was phosphorylated at a given point. MS/MS also can be used to determine the phosphorylation site as well as confirm the selectivity of the affinity isolation. For this separation, the proteolytic produced peptides can be separated as described above.

Another application of the present inventive methods is in removal of background proteins present in high levels. A ubiquitous problem in proteomic analysis is that for any given sample, e.g. serum, cell culture, tissues, etc., some proteins that are expressed at a very high level are not of particular analytical interest. A flippant comment that has been made is that if there is something wrong with these housekeeping proteins, you are already dead. In serum, for example, these proteins include albumin, transferrin and immunoglobulins. For any proteomic analysis, contamination with keratin from the lab environment also can be problematic. Each different type of sample will have different sets of background proteins expressed at high levels. Even after selective fractionation, many of these proteins are present at such high levels that the complicate subsequent analysis. Consequently, the selective removal, or at least partial depletion, of these components is useful.

To some extent, this is auxiliary to the general strategy implied here; analytical focus should be made to specific subsets of the proteome that are defined by research requirements. This application, however, can be used in isolation or in combination with other methods for fractionating the sample of interest based on the analytical research objective. In combination with the U-PIT labeling procedure described above, this might be a viable approach to a fairly broad and generic proteomic analysis.

For this application, the proteins must be separated intact as described above. To remove unwanted components, affinity chromatography, either in a column format on bulk media such as beads or magnetic beads, or an immunoprecipitation-based method can be used in which a mixture of different affinity capture agents is present, such that one affinity capture agent is present one for each component. These capture agents can be any suitable agent that binds the unwanted component, such as, for example, an antibody. The antibodies of the present invention can be monoclonal or polyclonal antibodies or any other suitable type of an antibody, such as a fragment (Fab) or a derivative of an antibody, a single chain antibody (scFv), a synthetic homolog, or synthetic antibody mimics, such as fibronectins, aptamers, etc. See, e.g., Abbas et al., *Cellular and Molecular Immunology*, W. B. Saunders Company, Philadelphia, Pa. (1991). One consideration on such a cocktail approach is that the binding conditions should be similar for all the target components to be "scavenged". It is not, however, a requirement that the unwanted components be released under identical conditions because their subsequent analysis is not part of the analytical scheme.

Another application of the present inventive methods is in analysis of glycosylation of proteins. Analysis of glycosylation is very complex due to the heterogeneous nature of the specific glyco-forms at any one site of glycosylation. Regardless of how challenging the overall task is, removal of non-glycosylated peptides from the analytical environment and generation of accurate relative quantitative characterization of each glycopeptide present considerably simplifies the analysis.

There are a number of suitable affinity separation methods that can be used in the context of this application. For example, use of immobilized boronate has been shown to be useful for the isolation of glycoproteins and can be used for glycopeptides as well. Lectin affinity chromatography could also be applied. There is not a single lectin that will capture all glycopeptides, although an added degree of specificity can be introduced by using one, or several, specific lectins to capture a single type of glycopeptide. For exampe, Concanavalin A can be used to isolate N-linked glycopeptides, but not O-linked glycopeptides. There are also a range of different lectins with different selectivities that are suitable for use in the present inventive methods. In some cases, a mixed lectin bed can be used, although care has to be taken that all of the affinity interactions can be loaded and eluted under similar conditions. See Apffel et al., *J. Chromatgr. A.*, 750: 35–42 (1996).

One of skill in the art will appreciate that the procedure outlined above does not address a key question of identification and characterization of the glycosylation for a given protein. However, use of proteolytic digestion and MS/MS would clearly identify the site of glycosylation and the mass of the carbohydrate would eliminate some carbohydrate structures. MS/MS can also be used to confirm the presence of carbohydrate substructures and consequently as an added filter to augment the selectivity of the physical isolation.

For this application, as the characteristic that is being used to isolate the fraction interest is the carbohydrate rather than the peptide, the proteolytic produced peptides may be separated as described above.

Analysis of transcription factors is another application of the present inventive methods. Transcription factors are a class of proteins that bind to a promoter or to a nearby region of DNA to facilitate or prevent transcription initiation. These components are key components in the control system of the biological system and are obviously subject to a range of feedback mechanisms. Understanding the control of transcription is of interest in understanding the cells ability to adapt and respond to changes and external stimuli. In general, most, if not all, transcription factors utilize a "zinc finger" structure for recognition of specific DNA sequences of 5–9 residues.

To isolate all the transcription factors expressed by a cell, a number of affinity approaches can be used to present DNA sequences or analogues to the proteins in the system and only isolate those that bind with a threshold affinity. For example, an affinity media based can be used on a immobilized population of all possible 9-mer DNA sequences. This can be done in a fairly straightforward way by performing a solid phase synthesis and randomizing the base introduced at each synthetic step. The actual oligo length would have to be significantly longer than 9 to allow access to the sequence by protein binding structures in the sample. Another approach is to generate a homopolymer of a synthetic, unnatural nucleic acid base that binds relatively well to everything for use in place of a randomized sequence of natural DNA. In both cases, binding and elution conditions can be tuned to allow efficient capture and subsequent removal of non-specific binding of proteins by application of appropriately stringent washing conditions.

In the larger context of these experiments, isolation of either specific cells or specific subcellular organelles, such as the nucleus, and synchronization of the state of the cell population is necessary. For this separation, because the three dimensional structure of the zinc finger motif is key in the transcription factor recognition process, proteins must be separated intact as described above.

Yet another application of the present inventive methods is in analysis of membrane proteins, which play a key role in signal transduction and cell-cell communications by acting in a number of ways as signal conduits from one side of the membrane to the other. There is a specific chromatographic phase developed by Mibel Aguilar at Monash University that may be useful in isolating these proteins (Lee & Aguilar, *Adv. Chromatogr.*, 41: 175–201 (2001)). As mentioned above, this specific affinity interaction could be enabled and leveraged by combination with the U-PIT labeling procedure. For this application, interaction of the protein with a membrane is based on the presence of both charged and hydrophobic structures on a single protein and thus the proteins preferably are separated intact as described above.

Analysis of protein-protein interactions can also be accomplished using the present inventive methods. Characterization of protein-protein interactions constitutes one of the fundamental approaches to characterization of a proteome by mapping all of the interactions and constructing reaction pathways based on this and ancillary information. This has been done previously using such techniques as Yeast Two Hybrid, see Field et al., *Nature*, 340: 245–46 (1989); however, mass spectrometry-based methods are also available. These methods can be, for example, done in solution by allowing complexes between proteins to form in solution and then analyzing the resulting complexes by MS. This requires relatively simple, and in most cases artificial, experimental conditions. A more promising approach is to immobilize the target protein and determine the proteins that bind to it. See Mann et al., *Nature Genetics*, 20: 46–51 (1998); Gavin et al., *Nature*, 415(6868): 141–47 (2002); Ho et al., *Nature*, 415(6868): 180–3 (2002). Results from such an approach would be greatly enhanced by introducing the quantitative analysis capabilities that combination with U-PIT labeling would yield. Given a set of relative pure target proteins, a simple immobilization method could be used to produce a specific affinity phase for studying proteins that interact with the target protein.

An alternative embodiment of this would be using the affinity media described herein for transcription factors to initially bind transcription factors and then subsequently investigating proteins that bind to the transcription factors. For this application, the proteins must be separated intact as described above.

Another application of the present inventive methods is in analyzing post translations modifications, e.g., ubiquitination. A general approach using these methods for any specific post-translational chemical modification of a protein is suitable if that modification can be recognized and captured by the immune system machinery. For example, ubiquitination is a process that eukaryotic cells use to mark a protein for degradation by the proteomome by tagging that protein with ubiquitin. For analysis of a cell state, it would be advantageous in a number or research contexts to understand what proteins of which the cell needs to dispose. Following digestion and U-PIT labeling of a sample, those peptides that have ubiquitin attached to them can be selectively isolated through use of a specific affinity capture agent. As described previously, this could be a natural anti-ubiquitin antibody or a synthetic mimic of some kind.

Similarly for different types of peptide modifications, such as sulfation, methylation or pegylation, different affinity systems can be develop and used to isolate only those species of interest. It should be noted that, in these cases, the modified peptide can be recognized and captured, as opposed to isolation based on a property that depends on the structure of the intact protein, such as the proteins ability to bind to a specific substrate. For this separation, the proteolytic produced peptides can be separated as described above.

Accordingly, the present inventive methods can be used in vivo and in vitro for investigative or diagnostic methods, which are well known in the art. Of course, it is to be understood and expected that variations in the principles of invention herein disclosed can be made by one skilled in the art and it is intended that such modifications are to be included within the scope of the present invention.

The examples that follow further illustrate the invention, but should not be construed to limit the scope of the invention in any way. Detailed descriptions of conventional methods, such as those relating to DNA, RNA and proteins, including antibodies, can be obtained from numerous publication, including Sambrook, J. et al., (1989) Molecular Cloning: A Laboratory Manual, $2^{nd}$ ed., Cold Spring Harbor Laboratory Press. All references mentioned herein are incorporated in their entirety.

EXAMPLES

Example 1

The present example demonstrates synthesis of 2-Ethylamino-4,6-Dichloro-s-Triazine (2). Ethylamine hydrochloride (0.44 g, 5.4 mmol) and 2,4,6-Trichloro-s-triazine (1,1 g, 5.4 mmol) were combined in a round bottom flask and cooled to −5° C. using an ice-salt bath. To the cooled, stirred solution was added N,N-diisopropylethylamine (1.88 mL, 10.8 mmol). The resultant yellow colored solution was stirred at −5° C. for 1 h, the solvents removed under reduced pressure, and the resultant residue was dissolved in 1:1 v/v of ethyl acetate and water. The organic layer was separated, washed with saturated solution of $NaHCO_3$, and dried over $Na_2SO_4$. The organic solvent was removed under reduced pressure to yield an orange colored solid. The solid was triturated with hexane to yield the product 2 as a yellow-orange powder (0.7 g) with a yield of 68%.

Example 2

The present example demonstrates synthesis of a substituted triazine (3).

2-Ethylamino-4,6-dichloro-s-triazine (2, 0.36 g, 1.88 mmol) prepared in Example 1 and ethanolamine hydrochloride (0.18 g, 1.88 mmol) were dissolved in 15 mL of absolute ethanol, and then N,N-diisopropylethylamine (0.65 mL, 3.76 mmol) was added. The solution was heated under reflux for about 20 h. The reaction solution was cooled to room temperate, the volatile components removed under reduced pressure, and the resultant residue was dissolved in 1:1 v/v of ethyl acetate and water. The organic layer was separated, washed with saturated solution of $NaHCO_3$, and dried over $Na_2SO_4$. The organic solvent was removed under reduced pressure to yield a pale yellow colored powder in a 41% yield.

The yellow colored powder was further purified by LC-MS using a preparative Zorbax SB-C18 column (9.4 mm×25 cm) with a flow rate of 4 mL/min. Solvent A was 0.1% trifluoroacetic acid (TFA) in water. Solvent B was 0.1% TFA in acetonitrile. A linear gradient was used for the initial 2 min. until 10% solvent B was reached. Solvent B was increased to 18% over the next 16 min., increased to 100% solvent B over a 1 min. interval, and the column was flushed with 100% solvent B for the next 6 min. The product 3 was collected in the 13–15 min. time interval as a white crystalline solid. ES-MS, m/z=218 $[M+M]^+$ and the isotope pattern consistent with 1 chlorine atom present was observed.

Example 3

The present example also demonstrates synthesis of a substituted triazine (4). Compound 3 (30 mg, 0.276 mmol) synthesized and purified in Example 2 was dissolved in 10 mL of dry n-propanol, and then (2-aminoethyl)trimethylammonium chloride (50 mg, 0.276 mmol) and N,N-diisopropylethylamine (50 μL, 0.276 mmol) were added. The solution was heated under reflux for 2.5 days. The volatile components were removed under reduced pressure, and the residue was placed under high vacuum for several hours, usually 5–8 h. The residue thus obtained was dissolved in the minimal amount of water, and the solution was passed through a Bakerbond™ spe Octadecyl (C18) disposable extraction cartridge (J. T. Baker, Phillipsburg, N.J.) containing one gram of media. The cartridge was initially washed with water to remove salts and base, and the product was subsequently flushed from the column with 50%–100% acetonitrile/water solvent mixtures. The collected solvents were evaporated to yield 60 mg of 4 as a white crystalline film (75% yield). The product was identified by its fragmentation pattern in ES-MS, m/z=284 [M+].

Example 4

The present example demonstrates synthesis of another substituted triazine (5).

Compound 4 prepared in Example 3 was dissolved in 5 mL of dry dioxane. Separately, a suspension was prepared by placing N,N'-disuccinimidyl carbonate (DSC, 0.31 g, 1.2 mmol) in 8 mL of dry acetone. The suspension was added to the dioxane solution, followed by the addition of N,N-diisopropylethylamine (210 μL, 0.2 mmol). After approximately 20 min., a clear solution begins to form. The solution was stirred under a nitrogen atmosphere for 20 h at room temperature. The volatile components were removed under reduced pressure, and the residue was placed under high vacuum for several hours, usually 5–8 h. The residue thus obtained was highly water soluble.

The residue was purified on a LC-MS using polyhydroxyethyl A (4.6 mm×10 cm, 5 μm/20 nm pore), a hydrophobic interaction column obtained from PolyLC, Inc. (Columbine, Md.). Solvent A was 10 mM ammonium formate. Solvent B was 10 mM ammonium formate in acetonitrile: water (9:1 v/v). A linear gradient was used to decrease the initial 100% solvent B to 50% solvent B in 15 min. Then solvent A was increased to 100% over 1 min, and the column flushed with solvent A for an additional minute. The desired product 5 was collected in the 7.5–8 min. time interval as a white crystalline solid. ES-MS, m/z=310 $[M-hydroxysuccinimate]^+$.

Example 5

The present example demonstrates tagging of peptides with a substituted triazine, Compound (5). Compound 5 (3 mg, 7 μmol), prepared in Example 4, was dissolved in 200 μL of pH 7.8 100 mM phosphate buffer. Leucine enkephalin (1 μg, 1.4 μmol) was dissolved in 50 μL of the pH 7.8 phosphate buffer, and then added to the solution of compound 5. The colorless solution was gently shaken overnight at 30° C. The solution was then passed through a pasteur pipette filled with C18 media up to the 2 cm mark to remove the phosphate salts in the reaction solution, and then washed with methanol. The methanol was collected and analyzed with ES-MS. The m/z=865 $[M]^+$ is consistent with the presence of tagged-leucine enkephalin.

Example 6

The present example demonstrates tagging of peptides with a substituted triazine, Compound (6). Compound 6 was prepared as described in Examples 1–4, except ethyl-$d_5$-amine and ethanol-1,1,2,2-$d_4$-amine were used. Leucine enkephalin was tagged with the isotopically labeled compound 6 according to Example 5, and analyzed with ES-MS. The m/z=874 $[M]^+$ is consistent with the presence of isotopically tagged-leucine enkephalin.

Example 7

The present example demonstrates analysis of mixed samples of substituted triazines. Solutions containing leucine enkephalin tagged with the isotopically labeled compound 6 and non-isotopically labeled compound 5 were combined in a 3:1 ratio (labeled:unlabeled, v/v). The combined solution was then analyzed with ES-MS. The m/z=874 [M]⁺ and m/z=865 [M]⁺ are consistent with the presence of labeled and unlabeled tagged-leucine enkephalin.

What is claimed is:

1. A method for analyzing a peptide or peptides of interest, the method comprising:
   (a) fragmenting a first protein sample to form peptides therein;
   (b) fragmenting a second protein sample to form peptides therein;
   (c) labeling the peptides in the first protein sample with a first tag having the formula:

A-B-C wherein:
   A is an amine-reactive group having a succinimide or maleimide moiety;
   B is a triazine moiety defining a first detectable isotope label; and
   C is a charge replacement group;
   (d) labeling the peptides in the second protein sample with a second tag having the formula:

A-B-C wherein:
   A is an amine-reactive group having a succinimide or maleimide moiety;
   B is a triazine moiety defining a second detectable isotope label differing in mass from the first detectable isotope label; and
   C is a charge replacement group;
   (e) combining the labeled first and second protein samples and separating the peptide or peptides of interest from the combined first and second protein samples; and
   (f) determining the relative amount of the first detectable isotope label and the amount of the second detectable isotope label bound to the peptide or peptides of interest as a measure for analyzing the peptide or peptide of interest.

2. The method of claim 1, wherein the amine-reactive groups of the first and second tags are independently selected from the group consisting of:

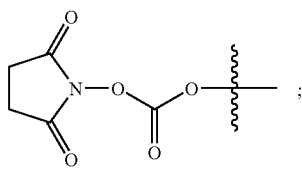

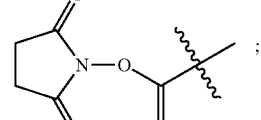

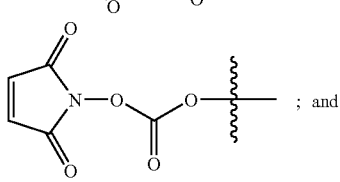 ; and

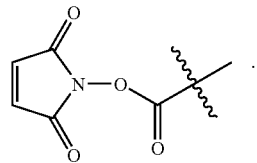

3. The method of claim 2, wherein said triazine moiety of the first tag is of the formula:

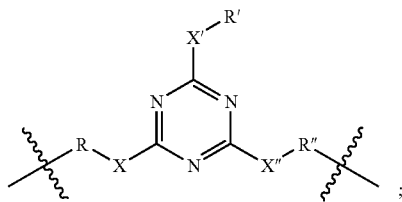

wherein:
R and R" each independently is alkyl, alkenyl, alkynyl, aryl or $(CZ_2CZ_2O)_n$ where n is from is 1 to 15 and each $Z_2$ independently H, $^2$H or $^3$H;
R' is hydrogen, alkyl, alkenyl, alkynyl or aryl;
X, X' and X" each independently is NH, O or S;
or X' and R' together may be H, $^2$H, $^3$H, $^{36}$Cl or $^{37}$Cl.

4. The method of claim 3, wherein the triazine moiety of the second tag is of the formula:

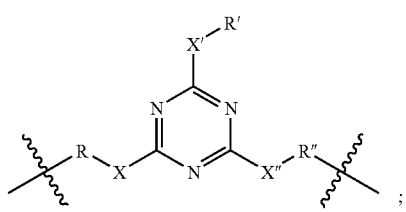

wherein:
R and R" each independently is alkyl, alkenyl, alkynyl, aryl, heteroaryl or $(CZ_2CZ_2O)_n$ where n is from 1 to 15 and each $Z_2$ is independently H, $^2$H or $^3$H;
R' is hydrogen, alkyl, alkenyl, alkynyl; aryl or heteroaryl;
X, X' and X" each independently is NH, O or S;
or X' and R' together may be H, $^2$H, $^3$H, $^{36}$Cl or $^{37}$Cl.

5. The method of claim 4, wherein the charge replacement groups of the first and second tags are of the formula:

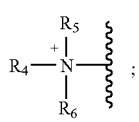

wherein each $R^4$, $R^5$ and $R^6$ is independently hydrogen, alkyl or aryl.

6. The method of claim 5, wherein X and X" are NH, and R and R" are alkyl.

7. The method of claim 6, wherein $R^4$, $R^5$ and $R^6$ are alkyl.

8. The method of claim 1, wherein separating the peptide or peptides of interest from the first protein sample and second protein sample comprises chromatographic separation.

9. The method of claim 1, wherein the determining the relative amount of the first detectable isotope label and the second detectable isotope label bound to the peptide or peptides of interest comprises mass determination.

10. The method of claim 1, wherein the first detectable isotope label and the second detectable isotope label have a mass difference of at least eight atomic mass units.

11. The method of claim 3, where, in the triazine moiety of the first tag, X' and R' taken together are H, $^2$H, $^3$H, $^{36}$Cl or $^{37}$Cl.

12. The method of claim 4, where, in the triazine moiety of the second tag, X' and R' taken together are H, $^2$H, $^3$H, $^{36}$Cl or $^{37}$Cl.

13. The method of claim 1, wherein fragmenting the first protein sample and the second protein sample comprises proteolytic cleavage.

14. A method for analyzing a peptide or peptides of interest, the method comprising:
   (a) fragmenting a first protein sample to form peptides therein;
   (b) fragmenting a second protein sample to form peptides therein;
   (c) labeling the peptides in the first protein sample with a first tag having the formula:

A-B-C wherein:
   A is an amine-reactive group selected from the group consisting of;

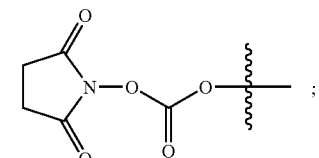

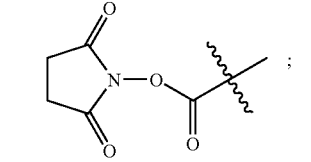

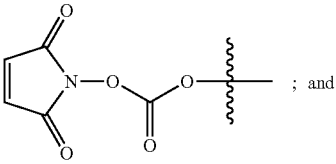 ; and

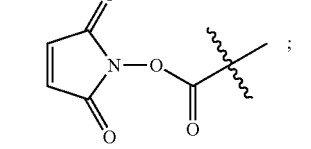

B is a triazine moiety defining a first detectable isotope label, the triazine moiety having the formula:

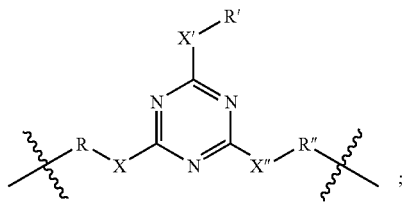

C is a charge replacement group of the formula:

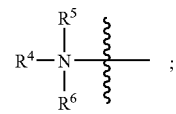

R and R" each independently is alkyl, alkenyl, alkynyl, aryl or $(CZ_2CZ_2O)_n$ where n is from 1 to 15 and each $Z_2$ is independently H, $^2$H or $^3$H;

R' is hydrogen, alkyl, alkenyl, alkynyl or aryl;

X, X' and X" each independently is NH, O or S;

or X' and R' together may be H, $^2$H, $^3$H, $^{36}$Cl or $^{37}$Cl;

$R^4$, $R^5$ and $R^6$ each independently is independently hydrogen, alkyl or aryl;

(d) labeling the peptides in the second protein sample with a second tag having the formula:

A-B-C wherein:
A is an amine-reactive group selected from the group consisting of

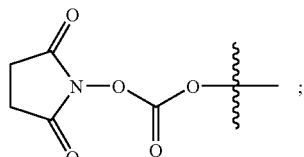

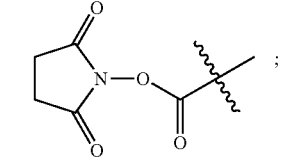

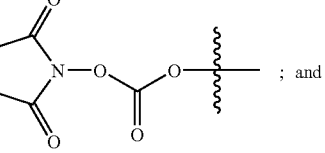 ; and

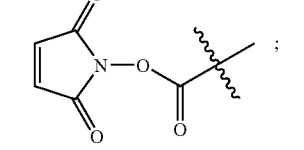

B is a triazine moiety defining a second detectable isotope label differing in mass from the first detectable isotope label, the triazine moiety having the formula:

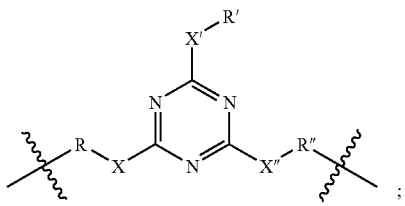

C is a charge replacement group of the formula:

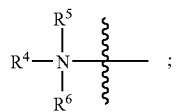

R and R" each independently is alkyl, alkenyl, alkynyl, aryl or $(CZ_2CZ_2O)_n$ where n is from 1 to 15 and each $Z_2$ is independently H, $^2$H or $^3$H;
R' is hydrogen, alkyl, alkenyl, alkynyl or aryl;
X, X' and X" each independently is NH, O or S;
or X' and R' together may be H, $^2$H, $^3$H, $^{36}$Cl or $^{37}$Cl;
$R^4$, $R^5$ and $R^6$ is independently hydrogen, alkyl or aryl;

(e) combining the labeled first and second protein samples and separating the peptide or peptides of interest from the combined first and second protein samples; and (f) determining the relative amount of the first detectable isotope label and the second detectable isotope label bound to the peptide or peptides of interest as a measure for analyzing the peptide or peptide of interest.

15. The method of claim 14, wherein the separating of the peptide or peptides of interest from the first protein sample and second protein sample comprises chromatographic separation.

16. The method of claim 14, wherein the determining of the relative amount of the first detectable isotope label and the second detectable isotope label bound to the peptide or peptides of interest comprises mass determination.

17. The method of claim 14, wherein the first detectable isotope label and the second detectable isotope label have a mass difference of at least eight atomic mass units.

18. The method of claim 14, where, in the triazine moiety of the first tag, X' and R' taken together are H, $^2$H, $^3$H, $^{36}$Cl or $^{37}$Cl.

19. The method of claim 14, where, in the triazine moiety of the second tag, X' and R' taken together are H, $^2$H, $^3$H, $^{36}$Cl or $^{37}$Cl.

20. The method of claim 14, wherein the fragmenting of the first protein sample and the second protein sample comprises proteolytic cleavage.

* * * * *